(12) United States Patent
Selfridge (10) Patent No.: US 12,244,570 B2
(45) Date of Patent: Mar. 4, 2025

(54) INVISIBLE MIDDLEWARE FOR ASYNCHRONOUS COMMUNICATION

(71) Applicant: MatrixCare, Inc., Bloomington, MN (US)

(72) Inventor: Barrett Gordon Selfridge, Bloomington, MN (US)

(73) Assignee: MATRIXCARE, INC., Bloomington, MN (US)

( * ) Notice: Subject to any disclaimer, the term of this patent is extended or adjusted under 35 U.S.C. 154(b) by 626 days.

(21) Appl. No.: 17/643,512

(22) Filed: Dec. 9, 2021

(65) Prior Publication Data

US 2023/0188506 A1    Jun. 15, 2023

(51) Int. Cl.
*H04L 9/40* (2022.01)
*G16H 10/60* (2018.01)

(52) U.S. Cl.
CPC ........ *H04L 63/0414* (2013.01); *G16H 10/60* (2018.01); *H04L 63/0471* (2013.01)

(58) Field of Classification Search
CPC . H04L 63/0414; H04L 63/0471; G16H 10/60; G16H 40/20; G16H 40/67
See application file for complete search history.

(56) References Cited

U.S. PATENT DOCUMENTS

| | | | | |
|---|---|---|---|---|
| 10,447,779 | B2* | 10/2019 | Dieterich | H04L 67/01 |
| 10,499,313 | B2* | 12/2019 | Chen | H04L 45/28 |
| 11,178,091 | B1* | 11/2021 | Madhavan | H04L 47/50 |
| 11,582,320 | B2* | 2/2023 | Fujino | H04L 67/566 |
| 2008/0137855 | A1* | 6/2008 | Enomoto | H04L 69/161 |
| | | | | 709/227 |
| 2009/0049356 | A1* | 2/2009 | Lin | H04L 1/188 |
| | | | | 455/69 |
| 2009/0052319 | A1* | 2/2009 | Muqattash | H04L 47/83 |
| | | | | 370/230.1 |
| 2009/0222497 | A1* | 9/2009 | Ryan | G06F 8/65 |
| 2009/0279481 | A1* | 11/2009 | Garcia | H04L 45/28 |
| | | | | 370/328 |
| 2012/0042077 | A1* | 2/2012 | Ceccarelli | H04L 45/00 |
| | | | | 709/226 |
| 2014/0032730 | A1* | 1/2014 | Fall | H04L 67/02 |
| | | | | 709/223 |
| 2014/0237021 | A1* | 8/2014 | Lamb | H04L 69/163 |
| | | | | 709/203 |
| 2019/0109713 | A1* | 4/2019 | Clark | G06F 16/182 |
| 2019/0109821 | A1* | 4/2019 | Clark | H04L 63/0414 |
| 2019/0341133 | A1* | 11/2019 | Harding | G16H 10/60 |
| 2020/0344222 | A1* | 10/2020 | Manges | H04L 67/34 |
| 2022/0130535 | A1* | 4/2022 | Sobti | G16H 40/67 |

* cited by examiner

*Primary Examiner* — Javier O Guzman
(74) *Attorney, Agent, or Firm* — Patterson + Sheridan, LLP (57) ABSTRACT

Embodiments herein describe middleware that serves as an intermediary between two computing systems performing asynchronous communication. Rather than communicating directly with each other, the two computing system communicate with the middleware; however, the middleware can be introduced seamlessly so that the two system believe they are communicating with each other rather than the middleware—i.e., the middleware is invisible to the systems. Asynchronous communication with guaranteed delivery may require the two computing systems to perform a handshake operation where the computing system transmitting the object does not consider the task complete until receiving a confirmation from the receiving computing system that the object was processed successfully.

20 Claims, 7 Drawing Sheets

ASYNCHRONOUS COMMUNICATION SYSTEM 100

INVISIBLE MIDDLEWARE FOR ASYNCHRONOUS COMMUNICATION

BACKGROUND

Field

Aspects of the present disclosure relate to middleware for enabling asynchronous communication between disparate computing systems.

Description of the Related Art

Asynchronous communication, unlike synchronous communication, separates the transmission of a request for an object to be processed by a second computing system from the completion of that request. As an example of synchronous communication, a first computing system may transmit an object or request to a web server (e.g., a second computing system) which the web server then processes and sends results back to the first computing system. The first computing system waits until it receives the results before considering the transaction complete. In asynchronous communication, the second computing system first sends an acknowledgment back to the first computing system when it successfully receives the object or the request to process an object, even before the second computing system has processed the object or request. Sometime later (which can be minutes, hours, or days), the second computing system can send a second confirmation to the first computing system indicating the object or request was successfully (or unsuccessfully) processed. In this manner, in asynchronous communication, the transaction is divided into transmission and processing phases which are treated separately unlike in synchronous communication where the first computing system waits for the entire transaction to occur before transmitting an acknowledgement.

Asynchronous communication is often used when transmitting large or important objects (e.g., documents, files, media, etc.) between two computing systems. For example, a first computing system may transmit an object to a second computing system and wait until it receives the confirmation from the second computing system that is received the object. Once the acknowledgement is received, the first computing system is then free to move on to other tasks while it waits for the second computing system to process the object and send another acknowledgment. However, the second computing system may be unavailable, or may be overloaded with receiving too many objects at once from the multiple computing system, and thus, may not send the first confirmation or acknowledgment. As such, asynchronous communication can result in unreliable communication.

SUMMARY

Certain embodiments provide a method that includes receiving, at middleware, an object from a first computing system where the object is destined for a second computing system and the first computing system, the middleware, and the second computing system are part of an asynchronous communication system. The method also includes transmitting a first confirmation from the middleware to the first computing system indicating the middleware successfully received the object, forwarding the object from the middleware to the second computing system, upon determining that the middleware did not receive a second confirmation that the second computing system successfully received the object, resending the object from the middleware to the second computing system, receiving a third confirmation from the second computing system indicating the second computing system successfully processed the object, and forwarding the third confirmation to the first computing system.

Another embodiment is a non-transitory computer readable medium comprising instructions to be executed in a processor, the instructions when executed in the processor perform an operation. The operation includes receiving, at middleware, an object from a first computing system where the object is destined for a second computing system and the first computing system, the middleware, and the second computing system are part of an asynchronous communication system. The operation also includes transmitting a first confirmation from the middleware to the first computing system indicating the middleware successfully received the object, forwarding the object from the middleware to the second computing system, upon determining that the middleware did not receive a second confirmation that the second computing system successfully received the object, resending the object from the middleware to the second computing system, receiving a third confirmation from the second computing system indicating the second computing system successfully processed the object, and forwarding the third confirmation to the first computing system.

Another embodiment is a system that includes a processor and a memory comprising instructions that, when executed by the processor, perform an operation. The operation includes receiving, at middleware, an object from a first computing system where the object is destined for a second computing system and the first computing system, the middleware, and the second computing system are part of an asynchronous communication system. The operation also includes transmitting a first confirmation from the middleware to the first computing system indicating the middleware successfully received the object, forwarding the object from the middleware to the second computing system, upon determining that the middleware did not receive a second confirmation that the second computing system successfully received the object, resending the object from the middleware to the second computing system, receiving a third confirmation from the second computing system indicating the second computing system successfully processed the object, and forwarding the third confirmation to the first computing system.

The following description and the related drawings set forth in detail certain illustrative features of one or more embodiments.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Embodiments herein describe invisible middleware that serves as an intermediary between two or more computing systems performing asynchronous communication. Rather than communicating directly with each other, the two computing systems communicate with the middleware; however, the middleware can be introduced seamlessly so that the two computing system believe they are communicating with each other rather than the middleware—i.e., the middleware is invisible to the computing systems. Stated differently, because the two computing systems can be using asynchronous communication before the middleware is added, adding the middleware does not disrupt the asynchronous communication between the two computing systems.

As mentioned above, asynchronous communication with guaranteed delivery may require the two computing systems to perform a handshake operation where the computing system transmitting the object does not consider the task complete until receiving a confirmation from the receiving computing system that the object was received successfully. That is, once the first computing system receives a confirmation that the second computing system successfully received the object, the first computing system is free to move on to other tasks without having to wait for another confirmation that the second computing system successfully processed the object. However, the receiving computing system may be unavailable or may become swamped or overloaded from too many requests from one, or multiple, computing systems. In one embodiment, the middleware receives the objects from the transmitting computing system and stores the objects in its queue. The middleware can then send a confirmation to the first computing system indicated the object was successfully received. This frees the first computing system to then perform other tasks (e.g., start another asynchronous communication) without having to wait for a confirmation from the receiving computing system.

The middleware also forwards the objects to the receiving computing system. If the middleware does not receive a confirmation from the receiving computing system, it can resend the objects until confirmations are received. Thus, if the receiving computing system is unavailable, only the middleware resends objects in a controlled manner to the receiving computing system, which prevents the computing system from being barraged with objects being resent from the transmitting computing system(s).

Further, the middleware may throttle the rate at which it forwards objects to the receiving computing system. For example, if the middleware receives objects from one or more transmitting computing systems at a rate that exceeds a maximum rate at which the receiving computing system can process the objects, the middleware can forward the objects at a reduced rate that meets (or is less than) the maximum rate of the receiving computing system. Doing so can prevent the receiving computing system from becoming overloaded.

Thus, the middleware can be used to reduce stress on and improve the availability of the two computing systems in an asynchronous computing system. Further, the middleware can be used in a system that initiates medical treatment and prophylactic remedies. For example, as part of prescribing a medication to a patient, a health provider can use a health portal (e.g., a first computing system) to send prescriptions or other medical treatments or prophylactic remedies to a pharmacy network (e.g., a second computing system). The invisible middleware can be used to improve the asynchronous communication between the health portal and the pharmacy network.

Figure 1:
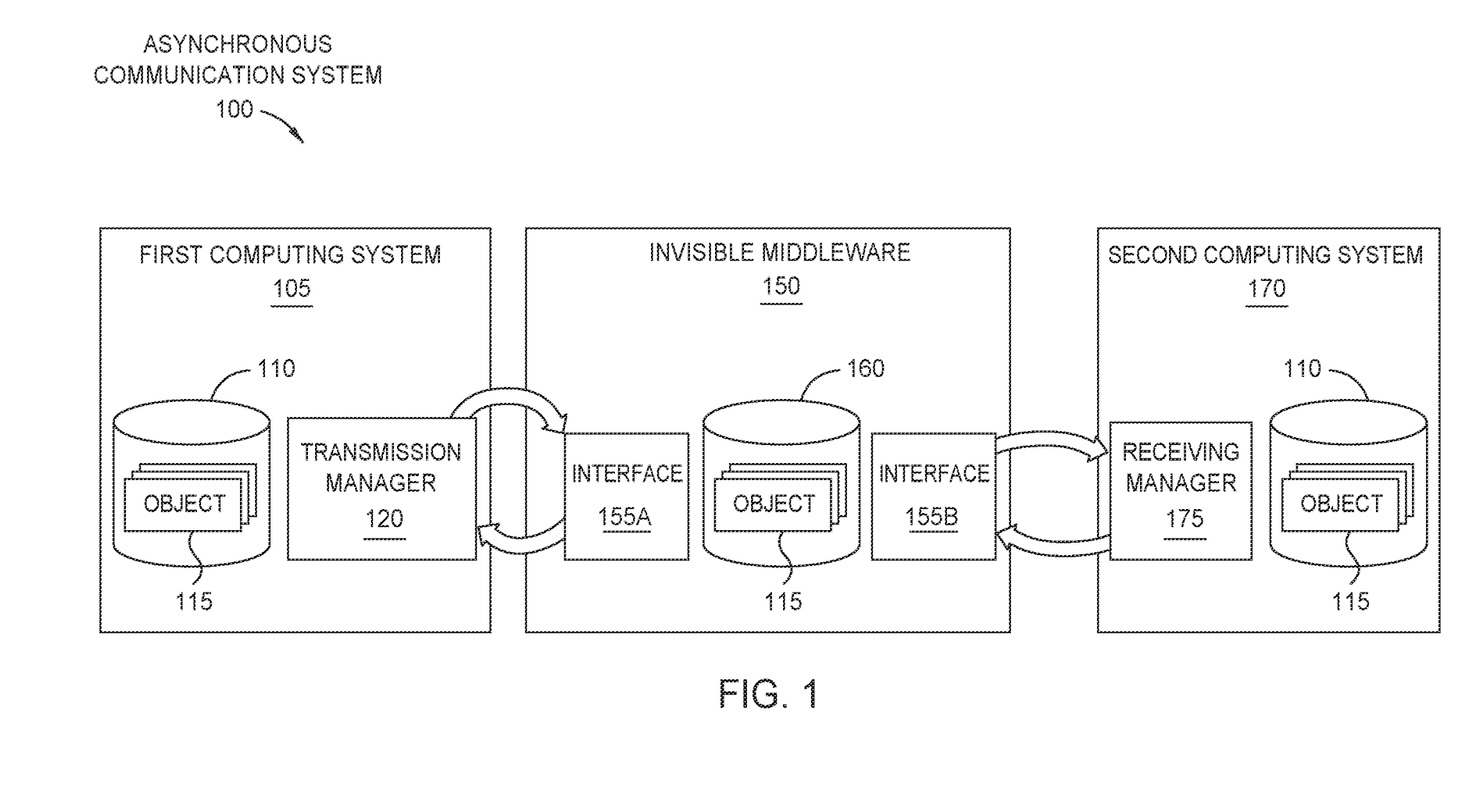
FIG. 1 depicts an asynchronous communication system with invisible middleware, according to one embodiment.

FIG. 1 depicts an asynchronous communication system 100 with invisible middleware 150, according to one embodiment. The asynchronous communication system 100 includes a first computing system 105 that performs asynchronous communication with a second computing system 170. To reduce the stress on the two systems 105, 170 and to improve their availability, the invisible middleware 150 is used to facilitate communication between the computing systems 105, 170.

The first computing system 105 includes a data repository 110 that stores objects 115. The data repository 110 represents any type of data storage element such as one or more hard drives, one or more storage servers, a data center, cloud computing storage, and the like. The objects 115 can be any data structure that is transmitted across a network (e.g., the internet) to the second communication system 170. The objects 115 can include documents (e.g., patient histories, prescriptions, orders, legal documents, etc.), media files (e.g., videos or images), folders, and the like. In the embodiments herein, the objects 115 are transmitted asynchronously through the network to the second computing system 170. The two computing systems 105, 170 may be different computing systems operated by different entities (e.g., a health care provider and a pharmacy network or a law firm and a court filing system).

Despite using asynchronous communication, the first computing system 105 may want to guarantee that the second computing system 170 received the transmitted objects 115. As such, the first computing system 105 may not consider a transaction complete until it has received a confirmation from the second computing system 170. If the second computing system 105 is unavailable for any reason (network is down, the system 105 is overloaded, system maintenance, etc.), the first computing system 105 may continue to resend the objects 115 until receiving a confirmation. This can further overwhelm the second computing system 105 and delay its return to normal operation.

Instead of permitting the first computing system 105 to directly communicate with the second computing system 170, the invisible middleware 150 (e.g., a software application or computing system) serves as an intermediary between the two computing systems 105, 170. As shown, the first computing system 105 includes a transmission manager 120 that transmits the objects 115 to an interface 155A in the invisible middleware 150. The middleware 150 can store the objects 115 in a queue 160 (e.g., hard drives, storage servers, database, data center, etc.) while forwarding the objects 115 to the second computing system 170 using an interface 155B. By queuing the objects 115, the middleware 150 retains a copy in case the objects 115 must be resent to the second computing system 170.

In one embodiment, when resending the objects 115, the middleware 150 can ensure it is not overloading the second computing system 170. That is, typically two computing system that use asynchronous communication do not have intelligence for throttling transmissions to the other but assume they can handle any number of requests. The middleware 150 provides intelligence to the asynchronous communication to reduce stress on the computing systems 105, 170.

When the middleware receives the objects 115 from the first computing system 105 it can immediately send a confirmation to the first computing system 105. That is, instead of waiting to determine whether the second computing system 170 received the object 115, the middleware 150 can send a confirmation to the first computing system 105 which then frees the first computing system 105 to perform other tasks. Transmitting the objects 115 from the first computing system 105 to the middleware 150 can be a synchronous communication that is part of the overarching asynchronous communication between the first and second computing systems 105, 170.

When forwarding the objects 115 to the second computing system 170, if the middleware 150 does not receive a confirmation from the second computing system 170, the middleware 150 takes on the role of re-transmitting the objects 115 to the second computing system 170, rather than the first computing system 105 in a traditional asynchronous communication link. Doing so permits the middleware 150 to insulate the second computing system 170 from being barraged by the first computing system 105 (and perhaps other computing systems) resending the objects 115. For example, when the middleware 150 does not receive a confirmation from the second computing system 170, the middleware 150 may resend the object 115, but it may do it at a different frequency than the first computing system 105 would resend the object 115 to the middleware 150. For instance, when not receiving the confirmation, the first computing system 105 may have resent the object 115 to the middleware 150 at a first frequency, but the middleware 150 may resend the object 115 to the second computing system 170 at a different, slower frequency. In one embodiment, the middleware 150 may resend the object 115 at the first frequency (i.e., the same frequency used by the first computing system 105 when resending the object 115), but after several iterations of not receiving a response, reduce the frequency at which it resends the object 115 to the second computing system 170. In this manner, the middleware 150 can control the number of times the object 115 is resent to the second computing system 170 when it is unavailable.

Once the object 115 is successfully received at the second computing system 170 (e.g., after a network failure or the second computing system 170 overcomes a system failure), a receiving manager 175 in the second computing system 170 forwards a confirmation to the middleware 150 which informs the middleware 150 that the object 115 was successfully received. However, the middleware 150 may not forward this confirmation to the first computing system 105. Instead, this confirmation is used to indicate that a synchronous communication between the middleware 150 and the second computing system 170 (which is part of the overarching asynchronous transaction between the first and second computing system 105, 170) is complete. In this manner, the middleware 150 can guarantee the transmission of the objects 115 from the first computing system 105 to a data repository 180 (e.g., one or more hard drives, one or more storage servers, a data center, or cloud computing environment) in the second computing system 170.

The second computing system 170 can process the received objects 115, after sending the confirmation to the middleware 150 indicating it successfully received an object 115. For example, the second computing system 170 may perform a data transform on the object 115 or forward the object 115 to a third computing system using synchronous communication. Once the second computing system 170 successfully processes the object 115 (or fails to successfully process the object 115), it can then transmit another confirmation to the middleware 150 to indicate to the first computing system 105 that the object 115 was successfully or unsuccessfully processed. This confirmation may be transmitted to the first computing system 105 seconds, hours, or even days after the first confirmation was sent from the middleware 150 to the first computing system 105. In the meantime, the first computing system 105 was free to perform other tasks while waiting on the second computing system 170 to process the object. After receiving the final confirmation, the first computing system 105 can then close the asynchronous transaction (if successful) or request that the second computing system 170 try again (if unsuccessful).

In FIG. 1 the middleware 150 is described as being invisible to the first and second computing system 105, 170 because from the perspective of these computing system 105, 170 it appears they are communicating with each other directly (i.e., without the use of an intermediary). That is, the middleware 150 does not interrupt the asynchronous communication protocols (e.g., the handshake) but is compatible with these protocols so that it can be easily added to the system 100 without having to modify the first and second computing systems 105, 170. Put differently, in order to enable the middleware 150 to serve as an intermediary, the first and second computing system 105, 170 do not have to be modified, which would be difficult to do since they may be operated by different entities. The middleware 150 could be added into the system 100 by the entity operating the first computing system 105 or by the entity operating the second computing system 170 without either computing system 105, 170 having to be modified.

For example, the entity operating the first computing system 105 may recognize that the first computing system 105 may overload or put undue stress on the second computing system 170. Instead of modifying the transmission manager 120, the entity can add the middleware 150 to the system 100 as an off-the-shelf solution. The transmission manager 120 can then be told to forward the objects 115 to a destination of the network corresponding to the middleware 150 rather than the second computing system 170. Further, when forwarding the objects 115 to the second computing system 170, the middleware 150 can indicate to the second computing system 170 that the confirmations should be transmitted to it rather than the first computing system 105.

In another example, the entity operating the second computing system 105 may add the middleware 150 to the system 100 because the first computing system 105 may send too many requests that can overload the second computing system 170. Instead of modifying or adding resources to the second computing system 170, the entity can add the middleware 150 to the system 100 as an off-the-shelf solution. The receiving manager 175 can then instruct the first computing system 105 (and any other computing system that it communicates with) to transmit the objects 115 to a destination in a network corresponding to the middleware 150. In this manner, the middleware 150 can be added by one entity without having to modify its computing system or ask another entity to modify its computing system. That is, the first and second computing systems 105, 170 can follow the same communication protocol and behave the same as they did before the middleware 150 was added, albeit the objects and confirmations are transmitted to the middleware 150 instead of directly to each other.

Figure 6:
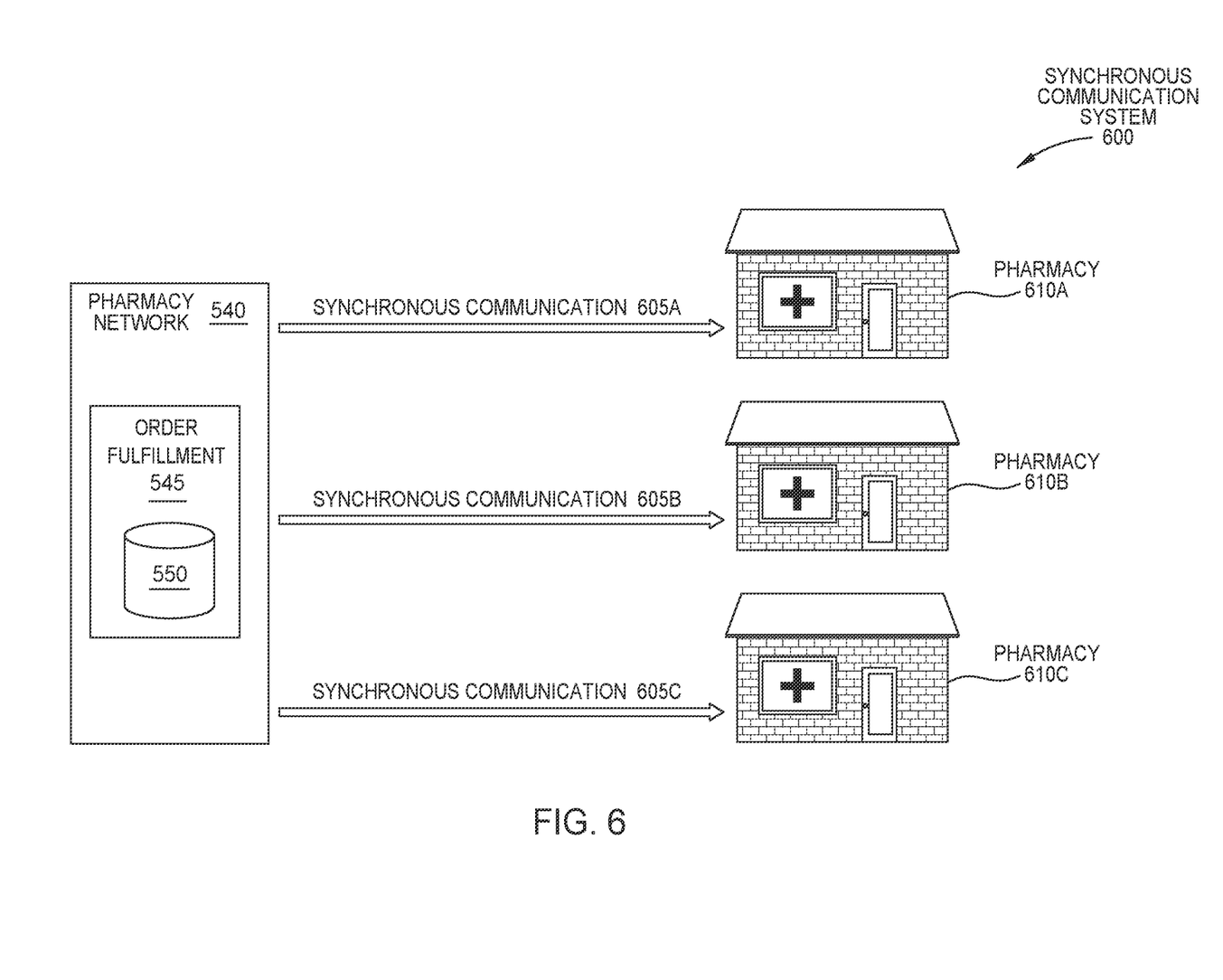
FIG. 6 illustrates a synchronous communication system, according to one embodiment.

As discussed in more detail in FIG. 6, the first computing system 105, middleware 150, and second computing system 170 can include one or more processors and memory. The processors are any electronic circuitry, including, but not limited to one or a combination of microprocessors, microcontrollers, application specific integrated circuits (ASIC), application specific instruction set processor (ASIP), and/or state machines, that communicatively couple to memory and control the operation of the first computing system 105, middleware 150, and second computing system 170. The processors are not limited to a single processing device and may encompass multiple processing devices.

The memory in the first computing system 105, middleware 150, and second computing system 170 may store, either permanently or temporarily, data, operational software, or other information for the processors. The memory may include any one or a combination of volatile or non-volatile local or remote devices suitable for storing information. The software represents any suitable set of instructions, logic, or code embodied in a computer-readable storage medium. For example, the software may be embodied in the memory, a disk, a CD, or a flash drive. In particular embodiments, the software may include an application executable by the processors to perform one or more of the functions described herein.

In one embodiment, the middleware 150 executes on a computing system that is separate from the first and second computing systems 105, 170 (e.g., a separate web server, data center, or cloud computing environment). These computing systems can then be interconnected using a private or public network. However, in another embodiment, the middleware 150 may be executed within one of the first and second computing systems 105, 170. For example, the middleware 150 may be installed in the first computing system 105 as an interface for the transmission manager 120 used to transmit the objects 115 on an external network (e.g., the internet) to the second computing system 170. In that example, the middleware 150 uses hardware resources in the first computing system 105 to execute its functions.

Figure 2:
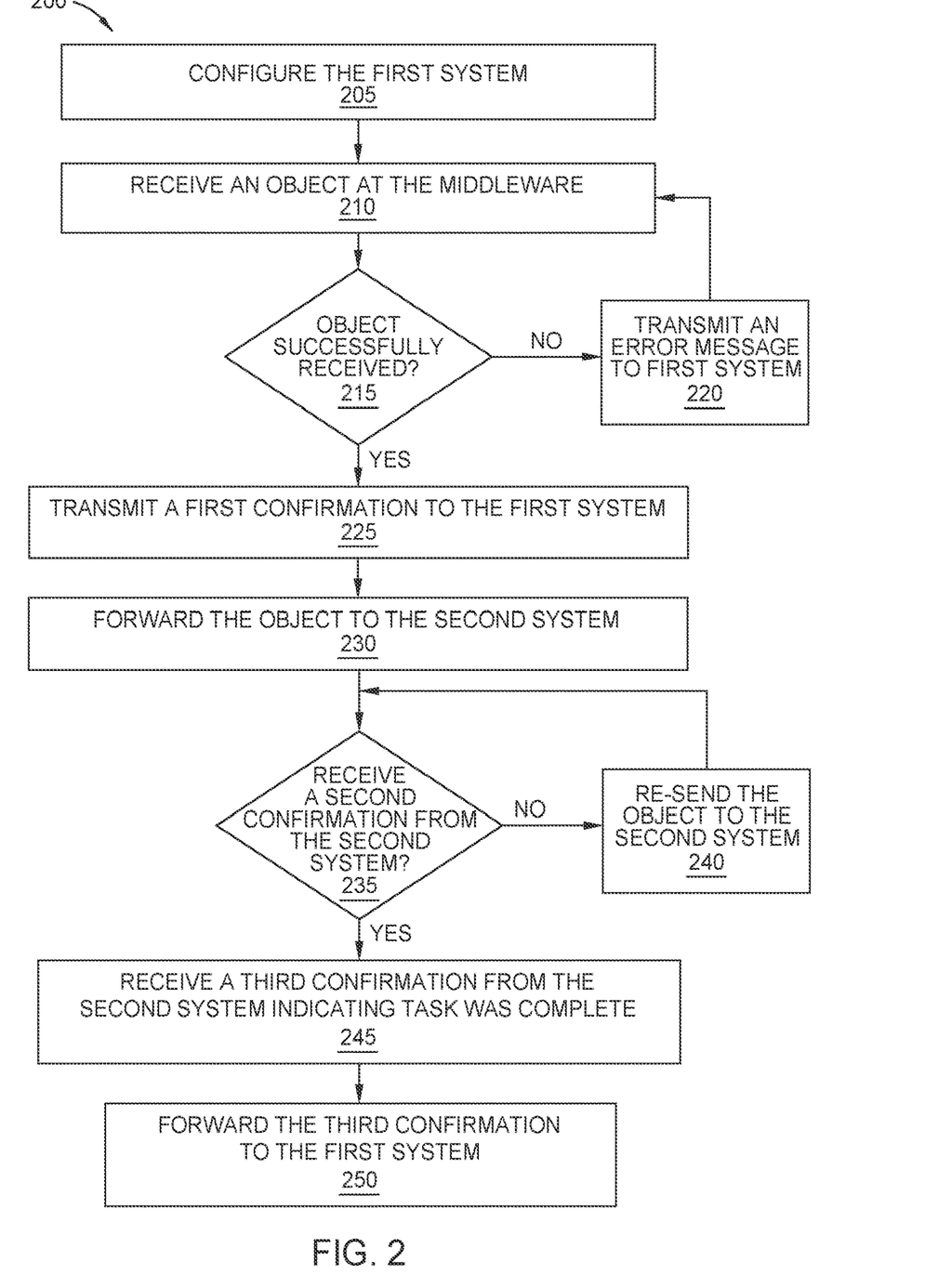
FIG. 2 is a flowchart for performing asynchronous communication using invisible middleware, according to one embodiment.

FIG. 2 is a flowchart of a method 200 for performing asynchronous communication using invisible middleware, according to one embodiment. At block 205, a system administrator configures a first computing system (e.g., the first computing system 105 in FIG. 1) to transmit objects to middleware (e.g., the middleware 150 in FIG. 1) rather than directly to a second computing system (e.g., the second computing system 170 in FIG. 1). For example, the middleware may have a different destination address in a network (e.g., a URL if http file transfers are used) than the destination of the second computing system. Thus, instead of transmitting objects to the second computing system, the first computing system instead transmits the objects to the middleware.

One advantage of the middleware is that it can be plugged into an asynchronous communication system without having to modify the first and second communication systems besides informing these systems to transmit objects and confirmations to the middleware. The middleware can continue to support any asynchronous communication handshaking protocols used by the computing system to guarantee delivery of the objects as described below.

At block 210, the middleware receives an object from the first computing system. Because the middleware may need to resend the object if the second computing system is currently unavailable, the middleware can store the object in a queue (e.g., temporary storage) until it has confirmed the second computing system successfully received the object. The queue could include a first in first out (FIFO) scheme to select in which order the objects stored in the queue are forwarded to the second computing system. However, the middleware could use other types of schemes to decide on how to select which objects are forwarded. For example, the middleware may prioritize the objects based on their type (some objects have greater priority) or based on which computing system sent the object to the middleware. For example, when objects are received from multiple computing systems, the middleware may assign different priorities to objects received from different computing systems.

At block 215, the middleware determines whether it successfully received the object from the first computing system. For example, there may have been a network failure that prevented the middleware from receiving the object.

In one embodiment, the transmission of the object from the first computing system to the middleware at block 210 is a synchronous transaction. As such, the first computing system may wait before moving on to performing other tasks until receiving a confirmation from the middleware that it successfully received the object. Thus, the synchronous transaction performed at block 210 is part of the overarching asynchronous transaction performed by the method 200. However, it is not a requirement that the communication between the first computing system and the middleware at blocks 210 and 215 be a synchronous transaction.

If the middleware did not receive the object, at block 220, the middleware transmits an error message to the first computing system. This can trigger the first computing system to re-send the object at block 215.

Once the object is received successfully, the method proceeds to block 225 where the middleware transmits a first confirmation to the first computing system. This indicates to the first computing system that this portion of the asynchronous communication is complete and it is free to perform other tasks while it waits for another confirmation indicating the second computing system was able to successfully process the object. For example, the first confirmation may close (or complete) a synchronous transaction between the first computing system and the middleware.

At block 230, the middleware forwards the object to the second computing system.

At block 235, the middleware determines whether it has received a second confirmation from the second computing system indicating the second computing system has successfully received the object. The second computing system may not receive the object for many different reasons, such as a temporary network failure, the second computing system is overloaded and was not able to process the object, or the second computing system is down for maintenance or due to a technical error.

If a second confirmation was not received, the method 200 proceeds to block 240 where the middleware resends the object (e.g., sends a duplicate of the object) to the second computing system. In one embodiment, the middleware resends the object according to a predefined interval (e.g., every minute) until a first confirmation is received. Advantageously, while the middleware is resending the object to the second computing system, the first computing system is free to perform other tasks. That is, in a traditional asynchronous transaction without the middleware, the first computing task would be responsible for re-sending the object. However, since the middleware has already sent the first confirmation to the first computing system, this system assumes the second computing system has already successfully received the object and thus is free to perform other tasks when in reality the second computing system may not have yet received the object. That is, because the first computing system may not know the middleware is there (i.e., it is invisible), the first computing system assumes that the second computing system has received the object.

In one embodiment, the middleware may resend the object to the second computing system at a different rate than the first computing system would resend the object to the second computing system if the middleware were not present in the asynchronous transaction. For example, the middleware may wait a longer time interval before resending the object after not receiving a response. Alternatively, in another embodiment, the middleware may first resend the object at an interval that meets (or exceeds) the interval used by the first computing system when resending the object but after continuing to not receive a first confirmation from the second computing system, increase the interval (reduce the frequency) used to resend the object. Doing so may reduce the stress on the second computing system if it is attempting to recover from an error or a backlog of requests. In this manner, the rate at which the middleware resends the object to the second computing system can be different from, or independent of, the rate the first computing system would use to resend the object to the second computing system.

Once the second computing system successfully receives the object, the middleware receives the second confirmation from the second computing system. Notably, the middleware does not forward the second confirmation to the first computing system. Instead, the second confirmation is only for the middleware to indicate that the transaction between the middleware and the second computing system is complete. In one embodiment, the middleware may use a synchronous transaction to transmit the object to the second computing system. That is, the middleware may wait until it receives the second confirmation from the second computing system before moving on to other tasks (e.g., seconding another object to the second computing system). Thus, in one embodiment, the communications between the first computing system and the middleware at block 210 and between the middleware and the second computing system may be two synchronous transactions that occur in the overarching asynchronous transaction described in the method 200. Thus, because the first synchronous transaction is complete when the middleware sends the first confirmation, the first computing system does not need to receive the second confirmation since this confirmation completes the second synchronous transaction between the middleware and the second computing system.

Once the middleware receives the second confirmation from the second computing system, the method 200 proceeds to block 245 where the middleware waits to receive a third confirmation from the second computing system indicating the task corresponding to the object was complete. This confirmation informs the first computing system that the object was successfully processed at the second computing system and the asynchronous transaction can be closed. In one embodiment, the second computing system sends the third confirmation to the middleware once the second computing system successfully processes the object (e.g., performed a data transform on the object, or forwarded the object to a downstream computing system using, e.g., synchronous communication) or fails to successfully process the object. For example, the second computing system may wait to send the third confirmation until a downstream synchronous communication has been performed.

Advantageously, the first computing system does not have to wait until the second computing system has completed its task or tasks before the first computing system can move on to other tasks. That is, after receiving the first confirmation, the first computing system can perform other tasks (e.g., initiate another asynchronous communication) while waiting for the third confirmation. Thus, the first computing system is not held up by the ability of the second computing system to performs its tasks—e.g., to complete a synchronous transaction, or to process the object.

Moreover, the middleware can delete the copy of the object it stored in its queue. Because the middleware may only store objects for current transactions, the size of its queue can be much smaller than the data repositories used by the first and second computing system (e.g., the data repositories 110 and 180 in FIG. 1).

At block 250, the middleware forwards the third confirmation to the first computing system. In response, the first computing system can close the asynchronous transaction or repeat the asynchronous transaction if it was unsuccessful. In addition to transmitting the third confirmation, in other embodiments, the middleware also receives a result from the second computing system from processing the object (e.g., from performing a data transform on the object or analyzing the object to provide an answer to a query). The middleware can forward this result to the first computing system along with the third confirmation.

Figure 3:
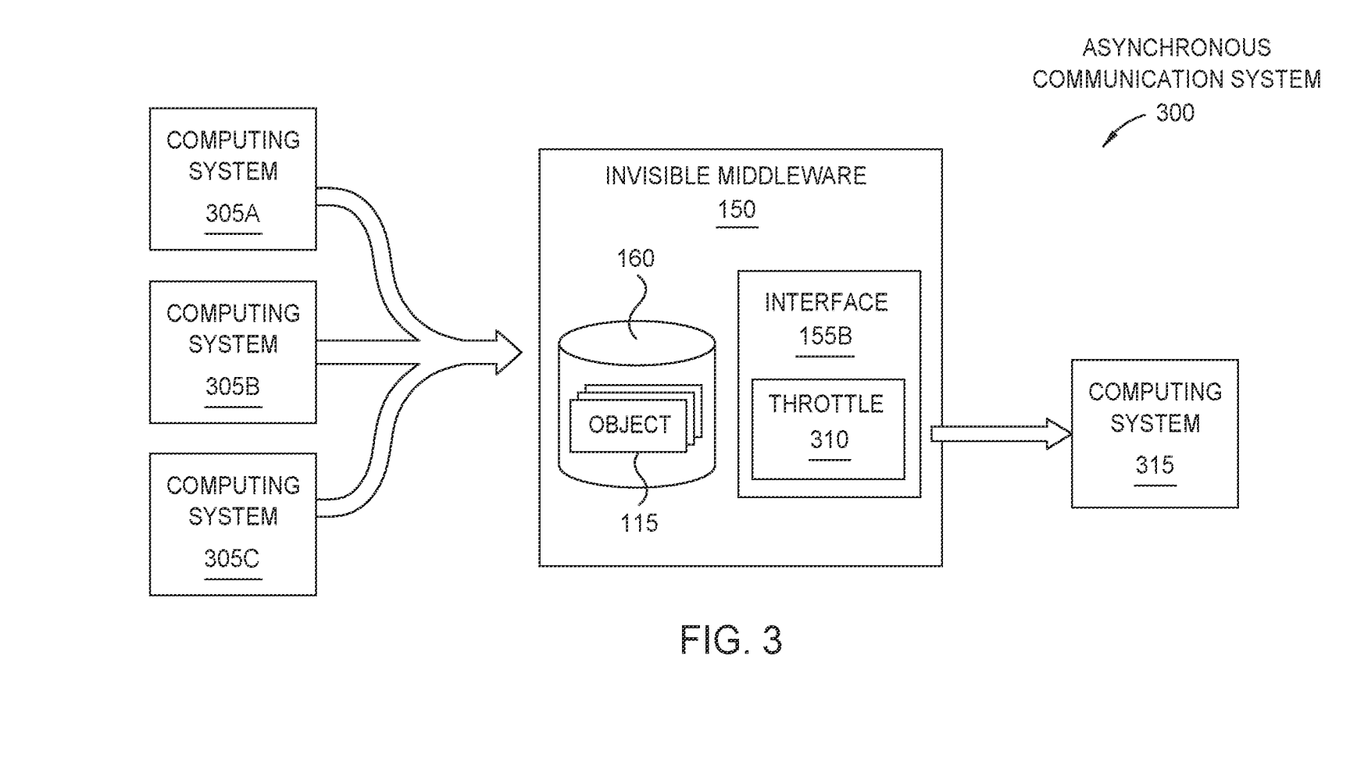
FIG. 3 depicts an asynchronous communication system with invisible middleware, according to one embodiment.

FIG. 3 depicts an asynchronous communication system 300 with invisible middleware 150, according to one embodiment. In this example, multiple computing systems 305A-C transmit objects to the middleware 150 which then forwards these objects to the computing system 315. That is, the computing system 315 receives objects from multiple, different computing systems 305.

Similar to FIG. 1, the middleware 150 includes the queue 160 for storing objects 115 received from the computing systems 305 and the interface 155B for forwarding those objects 115 to the computing system 315. The middleware 150 can then send confirmations to the respective computing systems 305 when the middleware 150 successfully receives the objects 115. Thus, the computing systems 305 are free to perform other tasks while waiting for the middleware 150 to forward the objects 115 to the computing system 315 and for the computing system 315 to process the objects 115.

In addition, the interface 155A in the middleware 150 includes a throttle 310 (e.g., a software application or module) which ensures the rate at which the middleware 150 forwards the objects 115 to the computing system 315 does not overwhelm or overload the computing system 315. In one embodiment, the throttle 310 ensures the objects 115 are forwarded at a rate that is not greater than a maximum rate that can be sustained by the computing system 315. The throttle 310 can evaluate the objects 115 in the queue 160 and determining whether forwarding the objects 115 would exceed the maximum rate. For example, if the middleware 150 has currently received five objects 115, but the maximum rate indicates the computing system 315 can handle receiving only three objects a given time period (e.g., within a ten second period), the throttle 310 may transmit three of the five objects 115 and wait ten seconds before transmitting the remaining two objects 115.

In one embodiment, the throttle 310 can also forward objects 115 to the computing system 315 at a faster rate than the middleware 150 is receiving objects 115 from the computing system 305. For example, assume the middleware 150 is currently receiving objects 115 at an average rate of two objects 115 every ten seconds. Also, the middleware 150 may have objects 115 stored in the queue 160 that were not forwarded to the computing system 315 from a previous time period when the rate at which the middleware 150 received objects 115 from the computing systems 305 was greater than the maximum rate at which the computing system 315 could receive the objects 115. Because the current rate at which the middleware 150 receives objects 115 is less than the maximum rate, the middleware can transmit both the current objects 115 received from the systems 305 as well as leftover queued objects 115 to the computing system 315. For example, the middleware 15 can receive objects at a rate of two objects every ten seconds but forward objects to the computing system 315 at a rate of three objects every ten seconds. Once the middleware has transmitted all the leftover objects in the queue 160, it can then reduce the rate used to forward objects 115 to the computing system 315 to match the rate at which the middleware 150 receives objects from the computing systems 305.

Thus, FIG. 3 illustrates an asynchronous communication system 300 where the middleware can prevent multiple transmitting computing systems 305 from overloading the receiving computing system 315. The middleware 150 is invisible to both the transmitting computing systems 305 and the receiving computing system 315 so that these systems do not have to be modified in order to install or plug in the middleware 150. Instead, the computing systems 305, 315 can simply be reconfigured to communicate with the middleware 150 rather than each other.

Further, while the system 300 illustrates multiple transmitting computing systems 305, the throttle 310 can also be used in an asynchronous computing system that includes only one transmitting computing system, like in FIG. 1. The throttle 310 can be used to ensure that the middleware 150 does not transmit objects received from the transmitting computing system at a rate that overloads the receiving computing system 315.

Figure 4:
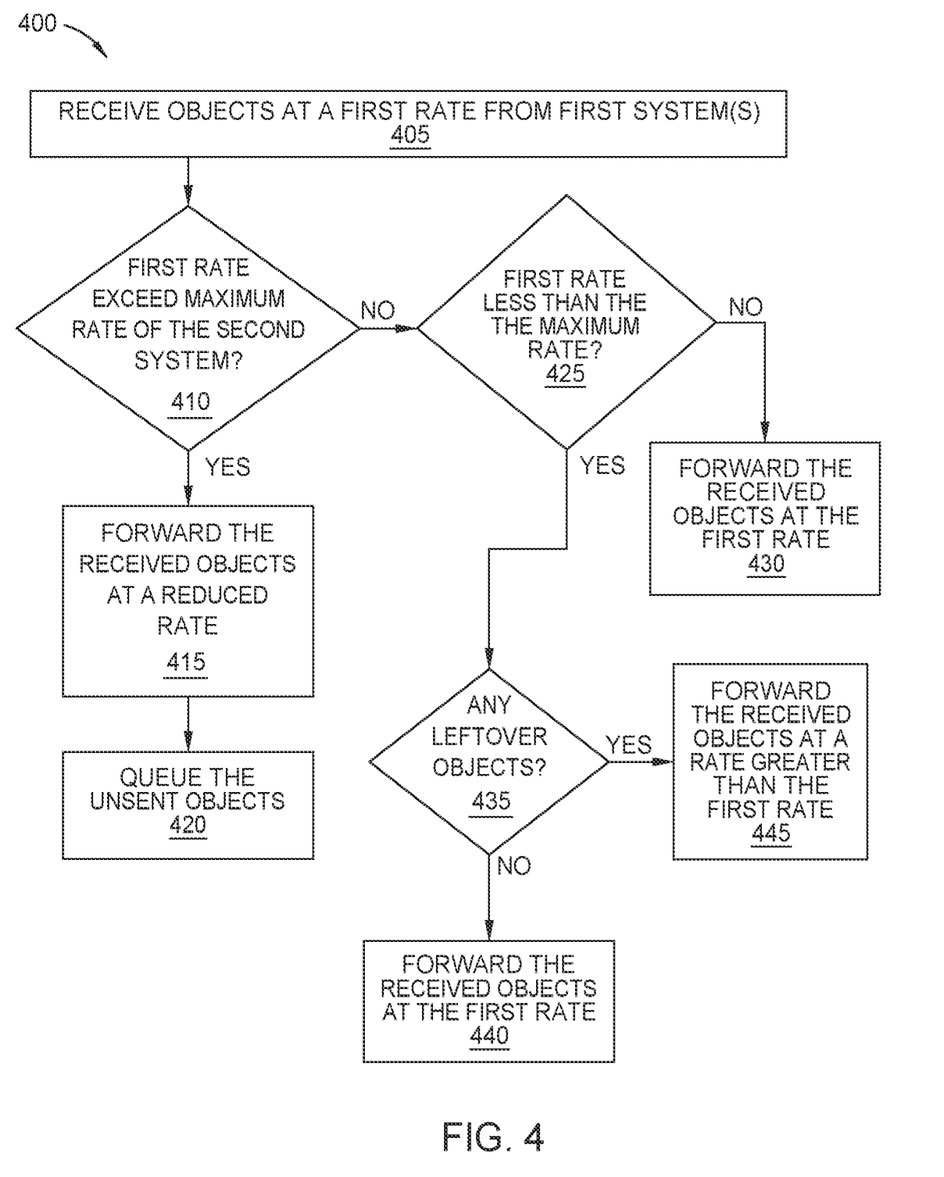
FIG. 4 is a flowchart for throttling data transmission in an asynchronous communication system using invisible middleware, according to one embodiment.

FIG. 4 is a flowchart of a method 400 for throttling data transmission in an asynchronous communication system using invisible middleware, according to one embodiment. At block 405, middleware receives objects at a first rate from a first computing system (like in FIG. 1) or from multiple computing systems (like in FIG. 3).

At block 410, the middleware determines whether the first rate exceeds a maximum rate of the second computing system that is the intended destination of the objects. For example, the middleware may query the second computing system to determine a maximum rate, or may receive a maximum rate from a system administrator of the second computing system. In another embodiment, the middleware may use predefined rate that is set without any knowledge of the second computing system. This predefined rate may be set conservatively to ensure it does not stress or overload the second computing system.

In another embodiment, the middleware may discover the maximum rate by forwarding objects at different rates to the second computing system and determine when the rate at which the second computing system transmits confirmations back to the middleware begins to slow down. For example, when forwarding objects at a rate of 10 objects (or less) every five seconds to the second computing system, the second computing system may return confirmations at a matching rate. However, when forwarding objects at a rate greater than 10 objects every five second, the second computing system may return confirmations at a slower rate than the objects are being sent, or at a reduced rate. These non-matching rates may indicate that the second computing system is struggling to keep up with the rate at which objects are being transmitted to it and is danger of becoming overloaded. The middleware may treat the rate of forwarding 10 objects every five seconds (or a slightly faster rate) as the maximum rate of the second computing system.

Assuming the first rate at which the middleware receives the objects exceeds the maximum rate of the second computing system, the method 400 proceeds to block 415 where the middleware forwards the received objects at a reduced rate that is at or below the maximum rate of the second computing system. For example, if the middleware receives objects at an average rate of 15 objects every five seconds and the maximum rate of the second computing system is 10 objects every five seconds, the throttle in the middleware can forward the received objects at a rate that is equal to (or less than) 10 objects every five seconds.

At block 420, the middleware queues the unsent objects. That is, the middleware can store the objects that were not immediately forwarded to the second computing system when throttling the rate. These queued, leftover objects can then be forwarded later as discussed below.

Returning to block 410, if the rate at which the middleware receives the objects does not exceed the maximum rate, the method 400 proceeds to block 425 where the middleware determines whether the first rate is below the maximum rate. If not, this means the first rate is equal to the maximum rate of the second computing system. In that case, at block 430, the throttle can forward the received objects at the first rate (which is the same as the maximum rate) to the second computing system. If there are queued, leftover items remaining from a time period when the first rate exceeded the maximum rate, the throttle may use a first-in-first-out (FIFO) scheme to transmit the received objects. That is, the throttle may first transmit the queued, leftover objects to the second computing system while queuing some or all of the currently received objects from the first computing system(s).

Returning to block 425, if the rate at which the middleware receives the objects is less than the maximum rate, the method 400 proceeds to block 435 where the middleware determines whether there are any leftover objects stored in the queue from a time period when the first rate exceeded the maximum rate. If not, the method 400 proceeds to block 440 where the throttle forwards the received objects at the first rate (which is less than the maximum rate) to the second computing system. Notably, the middleware can still store the forwarded objects in its queue as discussed in the method 200 in case there is a failure or error that prevented the second computing system from receiving the objects. That way, the middleware can resend the objects to the second computing system.

If, however, at block 435 the middleware determines there are leftover objects in the queue, the method proceeds to block 445 which the middleware forwards objects to the second computing system at a rate greater than the first rate. That is, because the middleware has both the currently receive objects as well as leftover objects to transmit to the second computing system, the throttle can increase the rate at which the middleware forwards the objects to the second computing system relative to the first rate—e.g., the current average rate at which the middleware receives objects from the first computing system(s). In this manner, the middleware can "catch up" during slower times when the rate at which objects are being received is less than the maximum rate of the second computing system.

In one embodiment, the middleware can use a FIFO approach to forward the currently received objects and the leftover objects to the second computing system. For example, the middleware may first transmit the leftover objects to the second computing system using the increased rate. Eventually, assuming the first rate remains below the maximum rate of the second computing system, the middleware will transmit all the leftover objects in the queue and can begin to immediately forward the received objects to the second computing system. In that scenario, the rate at which the middleware forwards the objects to the second computing system will eventually match the rate at which the middleware receives the objects from the first computing system(s).

Figure 5:
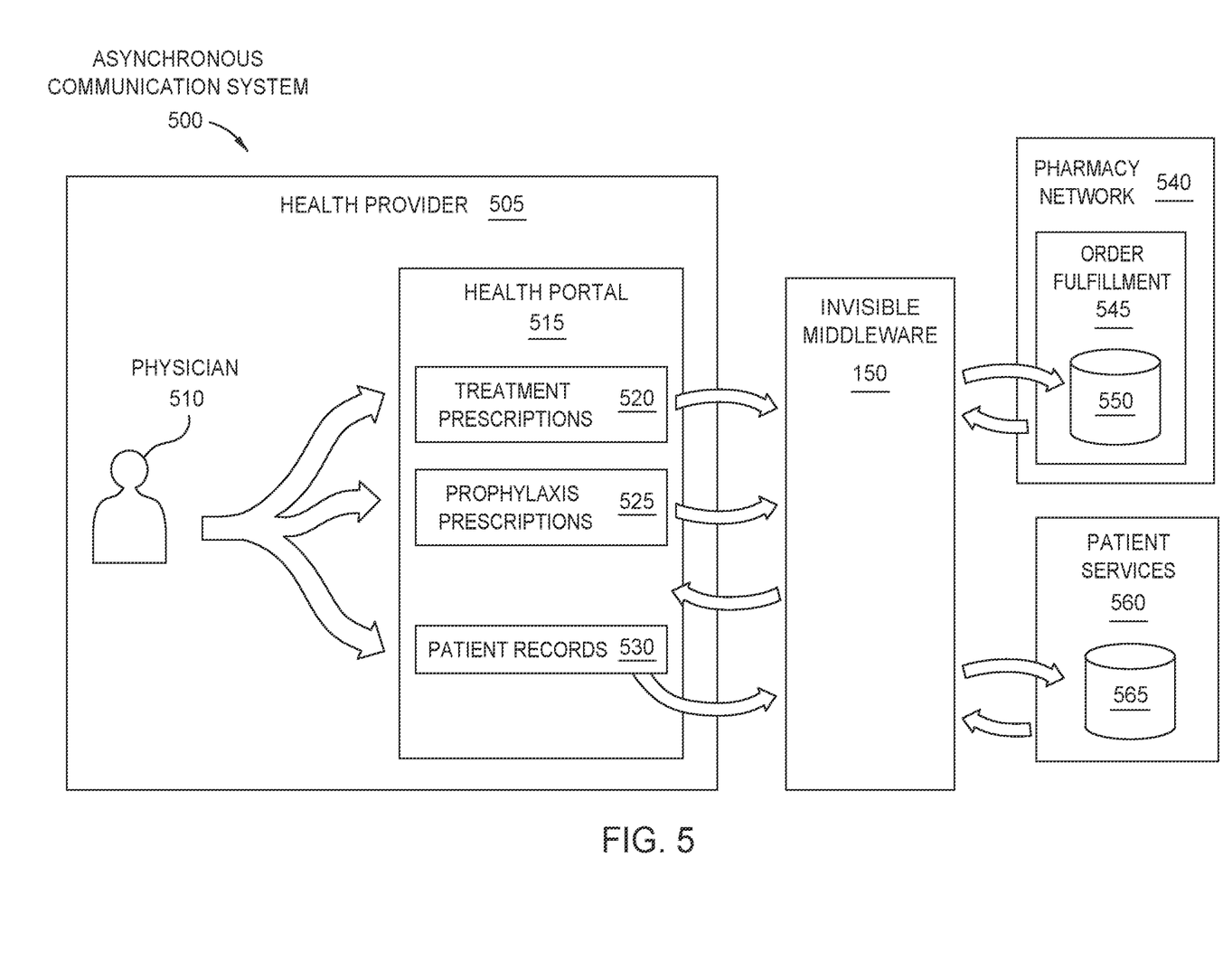
FIG. 5 depicts an asynchronous communication system with invisible middleware used in treatment and prophylactic actions, according to one embodiment.

FIG. 5 depicts an asynchronous communication system 500 with invisible middleware 150 used in treatment and prophylactic actions, according to one embodiment. As shown, a health provider 505 (e.g., a clinic, operation center, hospital, health network, etc.) uses asynchronous communication to transmit objects such as treatment prescriptions 520, prophylactic prescriptions 525, and patient records 530 to a third-party pharmacy network 540 and patient services 560. To facilitate this asynchronous communication, the system 500 includes the invisible middleware 150 discussed above in the previous figures and text.

As shown, the health provider 505 includes a physician 510 (or other authorized healthcare provider) that initiates treatment prescriptions 520 and prophylactic prescriptions 525, or updates/creates the patient records 530. In order to actually treat a patient, or provide a medical service to the patient, these objects are transmitted asynchronously to the pharmacy network 540 or patient services 560. For example, for the patient to obtain the prescriptions 520, 525, the health provider 505 forwards orders for the prescriptions 520, 525 to the pharmacy network 540. However, as mentioned above, the health provider 505 and the pharmacy network 540 may be two separate entities (e.g., two different companies) that use very different computing systems executing disparate software suites. Given the differences, asynchronous communication is used along with a confirmation or handshaking protocol to ensure the prescription orders were successfully received.

The middleware 150 can advantageously be used as an intermediary between a health portal 515 (e.g., a software application or a computing system) and the pharmacy network 540 (e.g., a software application or computing system). The middleware 150 can take responsibility for resending objects when there is a network failure or an outage in the pharmacy network 540 to resend the prescription orders as discussed in FIG. 2. Thus, problems with transmitting objects to the pharmacy network 540 do not affect the availability of the health portal 515. Further, the middleware 150 can throttle the number of prescriptions transmitted from the health portal 515 to the pharmacy network 540 so as not to overload the pharmacy network 540 as discussed in FIG. 4. While not shown, the middleware 150 can handle prescription requests from multiple health providers to prevent their respective health portals from overloading the pharmacy network 540.

Once the prescription orders are successfully stored in the middleware 150, it can transmits confirmations to the health portal 515, thereby freeing the health portal 515 to perform other tasks.

The middleware 150 can then forward those orders (e.g., using synchronous communication) to the pharmacy network 540 where they are stored in a data repository 550 in an order fulfillment application 545. The order fulfillment application 545 may then forward the prescription orders to a downstream pharmacy (e.g., the patient's preferred pharmacy). Unlike the asynchronous communication between the pharmacy network 540 and the health portal 515, communication between the pharmacy network 540 and the pharmacy may be synchronous communication. This is discussed in more detail in FIG. 6.

Advantageously, using asynchronous communication between the pharmacy network 540 and the health portal 515 means the health portal 515 does not have to wait until the pharmacy network 540 has received and processed the prescription orders (e.g., by forwarding them to the patient's pharmacy). That is, in this scenario, the health portal 515 does not have to wait for the middleware 150 to successfully forward the orders to the pharmacy network 540 and for the pharmacy network 540 to forward those order to a downstream pharmacy using synchronous communication. Instead, the health portal 515 is free to move to other transactions after receiving a confirmation from the middleware 150. Once the pharmacy network 540 has processed the prescription order—e.g., forwarded the orders to a pharmacy using synchronous communication—the pharmacy network 540 can update the health portal 515 using another confirmation (e.g., the third confirmation described in block 245 in the method 200). This may complete the asynchronous transaction.

FIG. 5 also illustrates using the middleware 150 to transmit the patient records 530 to patient services 560. In one embodiment, the patient services 560 may be operated by a different entity from the health provider 505. In another embodiment, the patient services 560 may be operated by the same entity as the health provider 505. In any case, due to the large size of the patient records 530, asynchronous communication is used to transmit the records 530 to the patient services. Because of the large size of the patient records 530, any transient network issues or brief errors in the patient services 560 can result in the patient services 560 not successfully receiving the records 530. The middleware 150 can alleviate the stress on the health portal 515 and the patient services 560 by taking responsibility for resending the patient records 530 during a failed transmission. As discussed above, the middleware 150 can retransmit the patient records 530 in a manner that reduces stress on the receiving computing system (e.g. the patient services 560) when it is attempting to recover from an error or from being overloaded as discussed in FIG. 2. Further, the middleware 150 can throttle the rate at which the patient records 530 are forwarded to the patient services 560 to prevent this computing system from becoming overloaded as discussed in FIG. 4.

In this manner, the middleware 150 can be used to provide medical treatment or prophylactic remedies to a patient. This can be in the form of transmitting prescriptions for medications or medical equipment to a pharmacy, or by transmitting patient records to a patient service which can then use those records to perform a medical treatment or provide prophylactic aid to the patient. However, the middleware 150 is not limited to a healthcare environment and can be used in any other asynchronous communication system such as, e.g., transmitting legal documents between a law firm's computing network to a court's docketing computing system or a user devices uploading large media files (e.g., photos or video) to a cloud storage network.

FIG. 6 illustrates a synchronous communication system 600, according to one embodiment. In one embodiment, the synchronous communication system 600 is downstream of the asynchronous communication system 500 in FIG. 5. In this example, the pharmacy network 540 receives the prescription orders from the middleware and stores them in the data repository 550. After (or while) forwarding confirmations to the middleware 150 (e.g., the second confirmation described at block 235 of the method 200), the pharmacy network 540 performs synchronous communications 605 to pharmacies 610. In one embodiment, the synchronous communications 605 include forwarding the prescription orders to the pharmacies 610.

In one example, the pharmacy network 540 may forward the prescriptions based on a preference of the patient. For example, Patient A may prefer to use the pharmacy 610A, and thus, the pharmacy network 540 can use synchronous communications 605A to forward the prescriptions for Patient A to pharmacy 610A. However, Patient B may prefer the pharmacy 610B. Thus, the pharmacy network 540 can use synchronous communications 605B to forward the prescriptions for Patient B to pharmacy 610B.

Advantageously, the healthcare provider 505 in FIG. 5 does not have to wait until the synchronous communications 605 between the pharmacy network 540 and the pharmacies 610 are complete before the healthcare provider 505 can move on to other tasks. That is, after receiving the first confirmation from the middleware, the healthcare provider 505 can perform other tasks (e.g., prepare and send other prescription orders to the pharmacy network 540) while waiting for the pharmacy network 540 to forward the prescription orders to the pharmacies 610 using the synchronous communications 605. The pharmacy network 540 can forward the prescription order to one of the pharmacies 610 using synchronous communication 605. In the meantime, the healthcare provider 505 is not held up waiting for the synchronous communication 605 to complete.

Once the synchronous communication 605 is complete, the pharmacy network 540 can forward another confirmation to the middleware (e.g., the third confirmation described at block 245 in the method 200). For example, after the pharmacy 610 receives a prescription order, it can send a confirmation to the pharmacy network 540 which completes the synchronous communication 605. In response, the pharmacy network 540 transmits a confirmation to the middleware, which forwards the confirmation to the healthcare provider. Once the healthcare provider receives the confirmation, the healthcare provider can close the asynchronous communication.

If the synchronous communication 605 failed, the pharmacy network 540 can transmit a confirmation to the middleware and healthcare provider indicating the synchronous communication failed. For example, the network between the pharmacy network 540 and the pharmacy 610 may be unavailable. If the synchronous communication 605 fails, this means the asynchronous communication also failed since, although the prescription order was successfully received at the pharmacy network 540, the prescription order was not ultimately received at the pharmacy 610. Thus, in this embodiment, when the synchronous communication 605 fails, the confirmation sent by the pharmacy network 540 to the middleware and the healthcare provider can indicate this failure. In response, the healthcare provider may restart the asynchronous communication. This can trigger the pharmacy network 540 to restart the synchronous communication 605.

In one embodiment, once the asynchronous communication has completed successfully, the healthcare provider can inform the patient that the prescription has been delivered to the pharmacy 610. The pharmacy can then use its own notification system to inform the patient when the prescription is available for pickup. For example, the asynchronous communication can provide the patient's contact information to the pharmacies 610. Thus, the pharmacies 610 can directly reach out to the patients to inform them when they can pick up their prescriptions. Thus, FIG. 6 illustrates how synchronous communications 605 can be performed in the context of an asynchronous communication. That is, as part of completing an asynchronous communication, a synchronous communication is performed.

In FIG. 6, the synchronous communication 605 may have to be completed first before the asynchronous communication can be completed. In one example, the third confirmation that is part of the asynchronous communication in method 200 indicates whether the synchronous communication between the second computing system and a downstream computing system was, or was not, successfully completed. However, other asynchronous communications may not include embedded synchronous communications.

Example Computing Hardware

Figure 7:
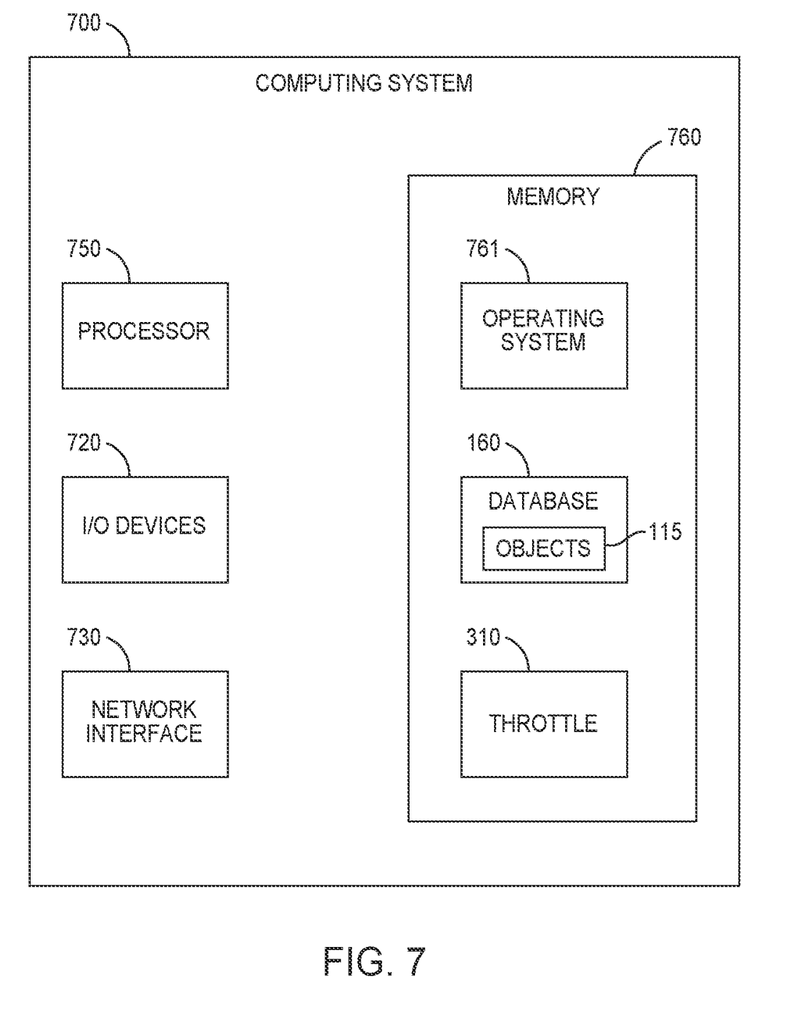
FIG. 7 illustrates a computing system, according to one embodiment.

FIG. 7 illustrates a computing system 700, which may be used to implement one of the computing systems 105, 170 or the computing system that includes the invisible middleware 150 in FIG. 1 (e.g., a computer, a laptop, a tablet, a smartphone, web server, data center, cloud computing environment, etc.), or any other computing device described in the present disclosure. As shown, the computing system 700 includes, without limitation, a processor 750 (e.g., a central processing unit), a network interface 730, and memory 760. The computing system 700 may also include an input/output (I/O) device interface connecting I/O devices 720 (e.g., keyboard, display and mouse devices) to the computing system 700.

The processor 750 retrieves and executes programming instructions stored in the memory 760 (e.g., a computer readable medium). Similarly, the processor 750 stores and retrieves application data residing in the memory 760. An interconnect facilitates transmission, such as of programming instructions and application data, between the processor 750, I/O device interface, storage, network interface 730, and memory 760. The memory 760 is generally included to be representative of volatile and non-volatile memory elements. For example, the memory 760 can include random access memory and a disk drive storage device. Although shown as a single unit, the memory 760 may be a combination of fixed and/or removable storage devices, such as magnetic disk drives, flash drives, removable memory cards or optical storage, network attached storage (NAS), or a storage area-network (SAN). The memory 760 may include both local storage devices and remote storage devices accessible via the network interface 730. In this example, FIG. 7 illustrates using the computing system 700 to execute the middleware, and thus, the memory 760 includes the database 160 that stores the objects 115 and the throttle 310. If the computing system 700 were instead used to implement the computing systems 105, 170, it could include the transmission manager 120, the receiving manager 175, the health portal 515, and the order fulfillment 545.

As shown, the memory 760 includes an operating system 761. The operating system 761 may facilitate receiving input from and providing output to various components. For example, the network interface 730 can be used to output the GUIs to display the tags along with their visual indicators. Further, the network interface can be used to provide GUIs to the authorized person and receive input from the person.

Further, the computing system 700 is included to be representative of a physical computing system as well as virtual machine instances hosted on a set of underlying physical computing systems. Further still, although shown as a single computing device, one of ordinary skill in the art will recognize that the components of the computing system 700 shown in FIG. 7 may be distributed across multiple computing systems connected by a data communications network.

The processor 750 can be any electronic circuitry, including, but not limited to one or a combination of microprocessors, microcontrollers, application specific integrated circuits (ASIC), application specific instruction set processor (ASIP), and/or state machines, that communicatively couples to memory and controls the operation of the database 160 and throttle 310. The processor 750 may be 8-bit, 16-bit, 32-bit, 64-bit or of any other suitable architecture. The processor 750 may include an arithmetic logic unit (ALU) for performing arithmetic and logic operations, processor registers that supply operands to the ALU and store the results of ALU operations, and a control unit that fetches instructions from memory and executes them by directing the coordinated operations of the ALU, registers and other components. The processor 750 may include other hardware that operates software to control and process information. The processor 750 executes software stored on the memory 760 to perform any of the functions described herein. The processor 750 controls the operation and administration of the database 160 and throttle 310 by processing information. The processor 750 is not limited to a single processing device and may encompass multiple processing devices.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method, comprising:
  receiving, at middleware, an object from a first computing system; wherein the object is destined for a second computing system; and wherein the first computing system, the middleware, and the second computing system are part of an asynchronous communication system, and wherein the first computing system is associated with a health provider;
  transmitting a first confirmation from the middleware to the first computing system indicating the middleware successfully received the object;

forwarding the object from the middleware to the second computing system;
upon determining that the middleware did not receive a second confirmation that the second computing system successfully received the object, resending the object from the middleware to the second computing system;
receiving a third confirmation from the second computing system indicating the second computing system successfully processed the object; and
forwarding the third confirmation to the first computing system, wherein the third confirmation indicates that health information was received by the second computing system and that a patient has access to medical treatment or prophylactic aid.

2. The method of claim 1, wherein, from a perspective of the first computing system, the first computing system appears to be communicating directly with the second computing system without using the middleware and, from a perspective of the second computing system, the second computing system appears to be communicating directly with the first computing system without using the middleware.

3. The method of claim 2, wherein the first confirmation indicates to the first computing system that it is free to move on to other tasks while waiting for the third confirmation, and wherein the second confirmation is not forwarded from the middleware to the first computing system.

4. The method of claim 3, further comprising, during a time when the middleware does not receive the second confirmation from the second computing system:
transmitting duplicates of the object at a first rate from the middleware to the second computing system, wherein the first rate is less than a second rate used by the first computing system to resend objects.

5. The method of claim 3, wherein the third confirmation indicates to the first computing system that an asynchronous transaction between the first computing system and the second computing system is complete.

6. The method of claim 1, further comprising:
receiving a plurality of objects at the middleware, the plurality of objects destined for the second computing system;
determining whether transmitting the plurality of objects to the second computing system will exceed a maximum rate at which the second computing system can receive data; and
upon determining that forwarding the plurality of objects would exceed the maximum rate, forwarding the plurality of objects to the second computing system at a transmission rate that is at or below the maximum rate.

7. The method of claim 6, wherein the plurality of objects is received at a first rate that is greater than the transmission rate, the method further comprising:
queuing objects of the plurality of objects at the middleware that are leftover from a result of transmitting the plurality of objects at the transmission rate that is less than the first rate;
determining, after queueing the objects, that the middleware receives a second plurality of objects at a second rate that is less than the maximum rate of the second computing system; and
forwarding the second plurality of objects and the queued objects to the second computing system at a third rate that is greater than the second rate but equal to or less than the maximum rate.

8. The method of claim 1, wherein the object contains the health information for providing the medical treatment or the prophylactic aid to the patient, wherein the object is generated by a physician in order to treat the patient.

9. A non-transitory computer readable medium comprising instructions to be executed in a processor, the instructions when executed in the processor perform an operation, the operation comprising:
receiving, at middleware, an object from a first computing system; wherein the object is destined for a second computing system; and wherein the first computing system, the middleware, and the second computing system are part of an asynchronous communication system, and wherein the first computing system is associated with a health provider;
transmitting a first confirmation from the middleware to the first computing system indicating the middleware successfully received the object;
forwarding the object from the middleware to the second computing system;
upon determining that the middleware did not receive a second confirmation that the second computing system successfully received the object, resending the object from the middleware to the second computing system;
receiving a third confirmation from the second computing system indicating the second computing system successfully processed the object; and
forwarding the third confirmation to the first computing system, wherein the third confirmation indicates that health information was received by the second computing system and that a patient has access to medical treatment or prophylactic aid.

10. The non-transitory computer readable medium of claim 9, wherein, from a perspective of the first computing system, the first computing system appears to be communicating directly with the second computing system without using the middleware and, from a perspective of the second computing system, the second computing system appears to be communicating directly with the first computing system without using the middleware.

11. The non-transitory computer readable medium of claim 10, wherein the first confirmation indicates to the first computing system that it is free to move on to other tasks while waiting for the third confirmation, and wherein the second confirmation is not forwarded from the middleware to the first computing system.

12. The non-transitory computer readable medium of claim 11, wherein the operation further comprises, during a time when the middleware does not receive the second confirmation from the second computing system:
transmitting duplicates of the object at a first rate from the middleware to the second computing system, wherein the first rate is less than a second rate used by the first computing system to resend objects.

13. The non-transitory computer readable medium of claim 9, wherein the operation further comprising:
receiving a plurality of objects at the middleware, the plurality of objects destined for the second computing system;
determining whether transmitting the plurality of objects to the second computing system will exceed a maximum rate at which the second computing system can receive data; and
upon determining that forwarding the plurality of objects would exceed the maximum rate, forwarding the plurality of objects to the second computing system at a transmission rate that is at or below the maximum rate.

14. The non-transitory computer readable medium of claim 13, wherein the plurality of objects is received at a first rate that is greater than the transmission rate, the operation further comprising:
- queuing objects of the plurality of objects at the middleware that are leftover from a result of transmitting the plurality of objects at the transmission rate that is less than the first rate;
- determining, after queueing the objects, that the middleware receives a second plurality of objects at a second rate that is less than the maximum rate of the second computing system; and
- forwarding the second plurality of objects and the queued objects to the second computing system at a third rate that is greater than the second rate but equal to or less than the maximum rate.

15. The non-transitory computer readable medium of claim 9, wherein the object contains the health information for providing the medical treatment or the prophylactic aid to the patient.

16. The non-transitory computer readable medium of claim 15, wherein the object is generated by a physician in order to treat the patient.

17. A system, comprising:
- a processor; and
- a memory comprising instructions that, when executed by the processor, perform an operation, the operation comprising:
  - receiving, at middleware, an object from a first computing system; wherein the object is destined for a second computing system; and wherein the first computing system, the middleware, and the second computing system are part of an asynchronous communication system, and wherein the first computing system is associated with a health provider;
  - transmitting a first confirmation from the middleware to the first computing system indicating the middleware successfully received the object;
  - forwarding the object from the middleware to the second computing system;
  - upon determining that the middleware did not receive a second confirmation that the second computing system successfully received the object, resending the object from the middleware to the second computing system;
  - receiving a third confirmation from the second computing system indicating the second computing system successfully processed the object; and
  - forwarding the third confirmation to the first computing system, wherein the third confirmation indicates that health information was received by the second computing system and that a patient has access to medical treatment or prophylactic aid.

18. The system of claim 17, wherein, from a perspective of the first computing system, the first computing system appears to be communicating directly with the second computing system without using the middleware and, from a perspective of the second computing system, the second computing system appears to be communicating directly with the first computing system without using the middleware.

19. The system of claim 18, wherein the first confirmation indicates to the first computing system that it is free to move on to other tasks while waiting for the third confirmation, and wherein the second confirmation is not forwarded from the middleware to the first computing system.

20. The system of claim 19, wherein the operation further comprises, during a time when the middleware does not receive the second confirmation from the second computing system:
- transmitting duplicates of the object at a first rate from the middleware to the second computing system, wherein the first rate is less than a second rate used by the first computing system to resend objects.

* * * * *